United States Patent
Luo

(10) Patent No.: US 6,316,192 B1
(45) Date of Patent: Nov. 13, 2001

(54) METHOD FOR ENRICHMENT OF UNIQUE DNA FRAGMENTS THROUGH CYCLICAL REMOVAL OF PCR ADAPTER ATTACHED TO DNA FRAGMENTS WHOSE SEQUENCES ARE SHARED BETWEEN TWO DNA POOLS

(75) Inventor: Jianhua Luo, 221 Buchanan Pl. #A3, Pittsburgh, PA (US) 15228

(73) Assignee: Jianhua Luo, Pittsburgh, PA (US)

( * ) Notice: Subject to any disclaimer, the term of this patent is extended or adjusted under 35 U.S.C. 154(b) by 0 days.

(21) Appl. No.: 09/268,505

(22) Filed: Mar. 11, 1999

(51) Int. Cl.[7] .............................. C12Q 1/68; C12P 19/34
(52) U.S. Cl. ........................ 435/6; 435/91.1; 435/91.2
(58) Field of Search ............................ 435/6, 91.1, 91.2

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,800,159 | 1/1989 | Mullis et al. . |
| 5,525,471 * | 6/1996 | Zeng ......................................... 435/6 |
| 5,565,340 * | 10/1996 | Chenchik et al. ................... 435/91.2 |
| 5,726,022 * | 3/1998 | Burmer .................................... 435/6 |
| 5,804,382 * | 9/1998 | Sytkowski et al. ...................... 435/6 |
| 5,827,658 * | 9/1998 | Liang ....................................... 435/6 |
| 5,853,991 * | 12/1998 | Wang et al. ............................. 435/6 |
| 6,017,701 * | 1/2000 | Sorge et al. ............................. 435/6 |

OTHER PUBLICATIONS

Bjourson et al., Appl. Environ. Microbiol. 58(7), 2296–2301, 1992.*

Chang, Y., Cesarman, E., Pessin, M.S., Lee, F., Culpeper, J., Knowles, D.M., and Moore, P.S. Identification of Herpesvirus—Like DNA Sequences in AIDS–Associated Kaporii Sarcoma. Science, 1994, 1865–1869, vol. 266, U.S.A.

Davis, M., Cohen, D.I., Nielsen, E.A., Steinmetz, M., Paul, W.E., Hood. L. Cell–Type–Specific cDNA Probes and the Murine I Region: The Localization and Orientation of Add. Proc. Natl. Acad. Sci. U.S.A. 1984, 2194–2198, 81, U.S.A.

(List continued on next page.)

*Primary Examiner*—Kenneth R. Horlick

(57) ABSTRACT

A method of rapid isolation and enrichment of the differences of DNA fragments between two pools of DNA. These methods feature a process of converting undesirable tester to driver, and then re-utilizing the converted "driver" in the repeats of subtraction to achieve double exponential elimination of undesirable tester sequence. Improvements include: i) bypassing the need of PCR amplification or physical separation of desirable tester from undesirable one in each repeat of subtraction, it eliminates the necessity of tester dilution in each repeat of subtraction; ii) utilizing the converted "driver" from each repeat of subtraction, it eliminates the need for re-introducing additional driver into hybridization in each repeat of subtraction. These methods typically include: a) attaching a specific PCR adapter to the 5' and 3' ends of a DNA fragment from one DNA pool to form "tester" (Step A); (b) tester is mixed with driver that is not attached to adapter; (c) the mixture undergoes denaturing, re-annealing, and is followed by removal of adapter from tester/driver heteroduplex by single strand DNA specific nuclease; d) the process of (c) is then repeated at least once.

14 Claims, 7 Drawing Sheets

OTHER PUBLICATIONS

Diatchenko, L., Lau, Y.F.C. Campbell, A.P., Chenchik, A., Moqadam, F., Huang, B., Lukyanov, S., Lukyanov, K., Gurskaya, N., Sverdlov, E.D., Siebert P.D., Suppression Subtractive Hybridization. Proc. Natl. Acad. Sci. 1996, 6025–6030, 93, U.S.A.

Duguid, J.R., Dinauer, M. Library Subtraction of In Vitro cDNA Libraries to Identify Differentially Expressed Genes in Scrapie Infection. Nucl. Acids Res. 1992, 2789–2792, 18, U.K.

Hara, E., Kato, T., Nakada, S., Sekiya, L., Oda, K. Subtractive cDNA Cloning Using Oliga(dt)30—Latex and PCR: Isolation of cDNA Clones Specific to Undifferentiated Human Embryanal Carcinoma Cells. Nucl. Acids Res. 1991, 7097–7104, 19, U.K.

Hara, E., Yamaguchi, T., Tahara, H., Tsuyama, N., Tsurui, H., Ide, T., Oda, K: DNA—DNA Subtractive cDNA Cloning Using Oliga(dT)30—Latex & PCR: Identification of Cellular Genes Which are Overexpressed in Senescent Human Diploid Fibroblasts. Anal. Biochem. 1993, 58–64, 214, U.S.A.

Hendrick, D.M., Cohen, D.I., Nielsen, E.L., Davis. M. Isolation of cDNA Clones Encoding T Cell—Specific Membrane–Associated Proteins. Nature. 1984, 149–153, 308, U.K.

Hubank, M., Schatz, D.G. Identifying Differences in mRNA Expression by Representational Difference Analysis of cDNA. Nucl. Acids Res. 1994, 5640–5648, 22, U.K.

Kunkel, L.M., Monaco, A.P., Middles Worth, W., Oches, H.D. and Latt, S.A. Specific Cloning of DNA Fragments Absent from the DNA of a Male Patient With an X Chromosome Deletion. Proc. Natl. Acad. Sci. U.S.A 1985, 4778–4782, 82, U.S.A.

Lamar, Z.Z., Palmer, E. Y–Encoded, Species–Specific DNA in Mice: Evidence that the Y Chromosome Exists in Two Polymorphic Forms in Inbred Strains, Cell. 1984, 171–177, 37, MIT Press, U.S.A.

Liang, P., Pardez, A.B. Differential Display of Eukarytic mRNA by Means of the Molymerase Chain Reaction. Science. 1992, 967–971, 257, U.S.A.

Lisitsyn, U., Lisitsyn, N., Wigler, M. Cloning the Difference Between Two Complex Genomes. Science. 1993, 946–951, 259, U.S.A.

Nussbaum, R.L., Lesko, J.G., Lewis, R.A., Ledbetter, S.A., Ledbetter, D.H. Isolation of Anonymous DNA Sequence From Within a Submicroscopic X Chromosomal Delection in a Patient with Choroiderium Deafness, and Mental Retardation. Proc. Natl. Acad. Sci. U.S.A., 1987, 6521–6525, 84, U.S.A.

Sargent, T.D., Dawid, I. B. Differential Gene Expression in the Gastrula of *Xenopus laevis,* Science. 1983, 135–139, 222, U.S.A.

Straus, D., Ausubel, F.M. Genomic Subtraction for Cloning DNA Corresponding to Delection Mutations, Proc. Natl. Acad. Sci. U.&A. 1990, 1889–1893, 87, U.S.A.

Timblin, C., Battey, J., Kuehl, W.M. Application for PCR Technology to Subtractive cDNA Cloning: Identification of Genes Expressed Specifically in Murine Plasma Cytoma Cells. Nucl. Acids Res. 1990, 1587–1593, 18, U.K.

Wang, Z., Brown, D.D. A Gene Expression Screen. Proc. Natl. Acad. Sci, U.S.A. 1991, 11505–11509, 88, U.S.A.

Welsh, J., Chada, K., Dalal, S. S. Ralph, D., Cheng, L., McClelland, M. Arbitrarily Primed PCR Finger Printing of RNA. Nucl. Acids Res. 1992, 4965–4970, 20, U.K.

* cited by examiner

METHOD FOR ENRICHMENT OF UNIQUE DNA FRAGMENTS THROUGH CYCLICAL REMOVAL OF PCR ADAPTER ATTACHED TO DNA FRAGMENTS WHOSE SEQUENCES ARE SHARED BETWEEN TWO DNA POOLS

BACKGROUND

1. Field of the Invention

Cloning the DNA sequence that corresponds to a genomic defect has been essential to our understanding of the genetic cause of a disease. Identifying the mRNA species that are specific for a given tissue or for a specific event has been a foundation for many areas of modern biomedical research. If a unique sequence is present, or a common sequence is missed in a tumor tissue when it is compared with its normal counterpart, it can be used as a tumor marker. Finding unique DNA fragments in infectious tissue may help to identify infectious agents (Chang, Y., et al., 1994). To achieve these important goals, developing an efficient methodology to identify a sequence that is uniquely present in one sample in comparing with another has been a central issue.

2. Description of the Related Art

Although numerous methods that are designed to identify the differences in sequences have been reported (Davis 1984; Duguin et al., 1990; Hara et al., 1991; Hendrick et al., 1984; Kunkel et al., 1985; Lamar et al., 1984; Nussbaum, et al., 1987; Sargent et al., 1983), many of those methodologies involved physical separation between testers and drivers, such as hydroxyapatite chromatography (Timblin et al., 1990), a streptavidin-biotin interaction (Wang et al., 1991) or oligo(dT)-latex affinity chromatography (Hara et al., 1993). Generally speaking, these methods are time consuming and non-reproducible.

In the past 12 years, a method, known as polymerase chain reaction (PCR), was described (Mullis et al., U.S. Pat. Nos. 4,683,195, 4,683,202, 4,800,159). It is based on repeat cycling of denaturing the double-stranded DNA, oligonucleotide primer annealing to the DNA template, and followed by primer extension with a thermo-stable DNA polymerase. The PCR amplification process results in the exponential increase of a DNA fragment whose length is limited by the 5' ends of the oligonucleotide primers. Application of PCR to isolate and to analyze a particular DNA region requires knowledge of the DNA sequences flanking the region of interest. This feature generally limits its application to regions of known DNA sequence. In the past 5 years, a PCR-based technique, called representational difference analysis (RDA), employs a representational sampling approach by cutting the DNA into fragments based on its restriction enzyme cutting pattern, and attaching these restriction fragments to a PCR-adapter for PCR amplification. Subsequently, it employs a differential enrichment approach to identify and to enrich the differences between tested DNA samples without physical separation (Lisitsyn et al., 1993; Hubank et al., 1994). However, the protocol for this method was found very complicated and time consuming. It has been difficult to employ this technique for routine studies. The mRNA differential display (Liang et al., 1992) and RNA finger printing (Welsh et al., 1992) by randomly primed PCR on cDNA represent potentially faster and easier techniques to identify differential expression genes. However, high background and false positive results are frequently associated with these methods. These techniques also tend to bias toward those abundantly expressed sequences. Recently, a new PCR based cDNA subtraction technique, termed suppression subtractive hybridization (SSH), was described (Diatchenko et al., 1996). This technique used suppression PCR to preferentially amplify differential tester sequences to generate a cDNA probe library. Although this technique can dramatically enrich some differential DNA fragments, only one cycle of hybridization is permitted. Understandably, significant background may be present.

In view of the problems and limitations associated with the methods discussed above, there remains a strong need for a method with enhanced specificity, sensitivity, and efficiency of identifying the differences of DNA sequences between two samples. In this patent application, I describe a novel polymerase chain reaction (PCR)-reversal subtractive hybridization method that rapidly isolates unique DNA sequences present between two tissues or cell types while employing no physical separation between testers and drivers. This method, referred to as Differential Subtraction Chain (DSC), employs a "negative amplification" strategy to identify, and to enrich the differences between two populations of DNA. This strategy produces fast and efficient isolation of unique tester sequences with minimal background.

BRIEF SUMMARY OF THE INVENTION

The subject invention concerns methods of rapid isolation and enrichment of the differences of DNA fragments between two pools of DNA. These methods feature a process of converting undesirable tester to driver, and then re-utilizing the converted "driver" in the repeats of subtraction to achieve double exponential elimination of undesirable tester sequence. The subject invention represents two improvements over the methods disclosed by Yang et al. (1996), Lisitsyn et al. (1993), Straus et al. (1990) by: i) bypassing the need of PCR amplification or physical separation of desirable tester from undesirable one in each repeat of subtraction, it eliminates the necessity of tester dilution in each repeat of subtraction; ii) by utilizing the converted "driver" from each repeat of subtraction, it eliminates the need for re-introducing additional driver into hybridization in each repeat of subtraction. These methods typically include: a) attaching a specific PCR adapter to the 5' and 3' ends of a DNA fragment from one DNA pool to form "tester" (Step A); (b) tester is mixed with driver that is not attached to adapter; (c) the mixture undergoes denaturing, re-annealing, and followed by removal of adapter from tester/driver heteroduplex by single strand DNA specific nuclease; (d) process of (c) is repeated at least once.

BRIEF DESCRIPTION OF THE SEQUENCE

The SEQ ID No. for the nucleotide sequence of the adapters corresponds to the nucleotide sequence of the upper nucleotide strand shown in Table II.

SEQ ID NO. 1 is the nucleotide sequence of the adapter/primer HindIa

SEQ ID NO. 2 is the nucleotide sequence of the adapter HindIb.

SEQ ID NO. 3 is the nucleotide sequence of the adapter/primer HindIIa

SEQ ID NO. 4 is the nucleotide sequence of the adapter HindIIb

SEQ ID NO. 5 is the nucleotide sequence of the adapter/primer BgIa

SEQ ID NO. 6 is the nucleotide sequence of the adapter BgIb

SEQ ID NO. 7 is the nucleotide sequence of the adapter/primer BgIIa

SEQ ID NO. 8 is the nucleotide sequence of the adapter BgIIb

SEQ ID NO. 9 is the nucleotide sequence of the adapter/primer BamIa

SEQ ID NO. 10 is the nucleotide sequence of the adapter BamIb

SEQ ID NO. 11 is the nucleotide sequence of the adapter/primer BamIIa

SEQ ID NO. 12 is the nucleotide sequence of the adapter BamIIb

SEQ ID NO. 13 is the nucleotide sequence of the primer Oligo d(T)

SEQ ID NO. 14 is the nucleotide sequence of the adapter BgIIIG

SEQ ID NO. 15 is the nucleotide sequence of the primer BgIII

DETAILED DESCRIPTION OF THE INVENTION

A. Principles of Differential Subtraction Chain

Figure 1:
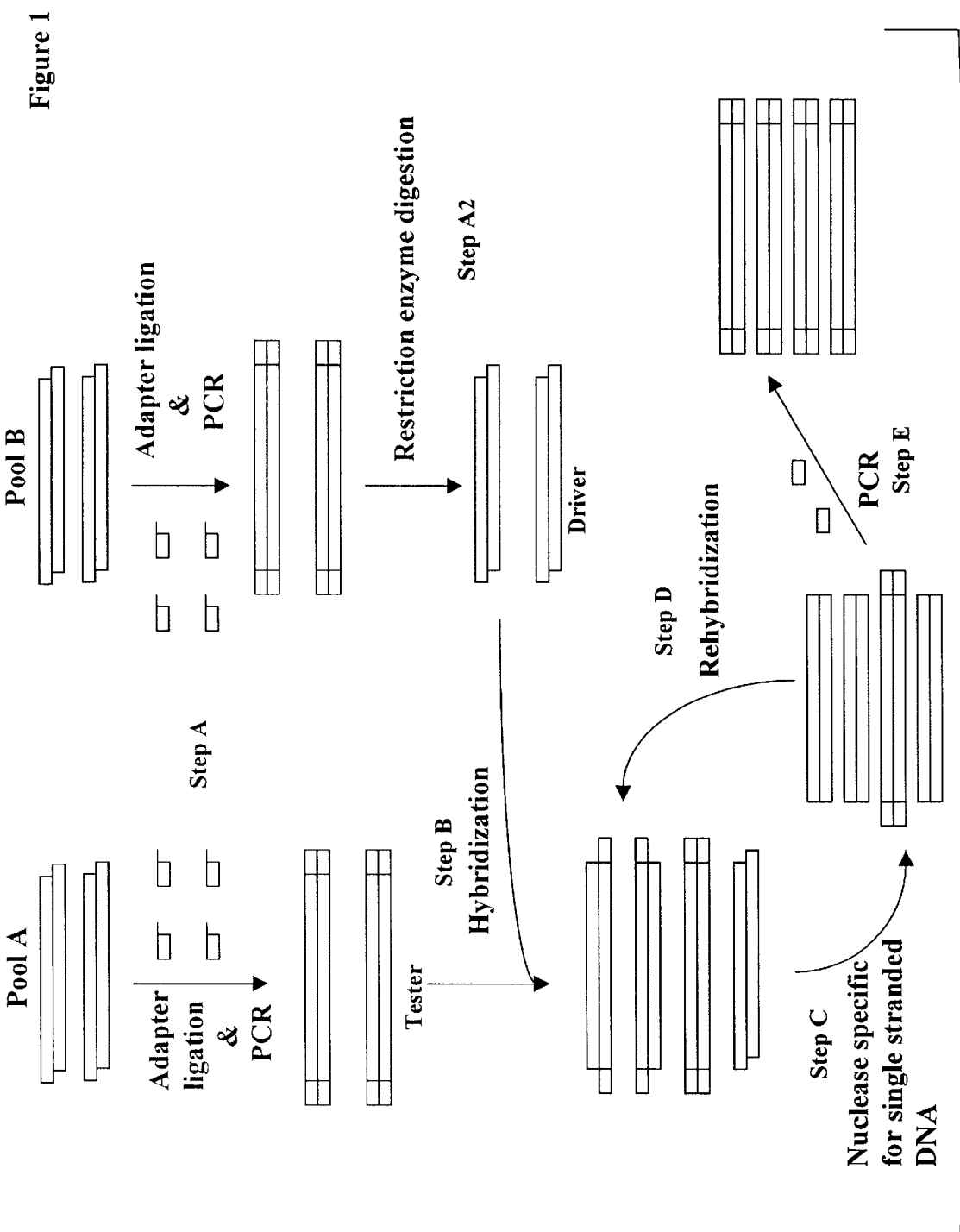
FIG. 1. Scheme of Differential Subtraction Chain when same adapter is used for Pool A and Pool B DNA. Pool A DNA is used as testers and Pool B as drivers. For pool B DNA, amplicons are digested with restriction enzyme to remove the adapters to become drivers before hybridization. In the DSC reaction, mixtures of testers and drivers are cycled repeatedly through hybridization and removal of single-stranded primers. An aliquot (5–10%) of DSC reaction stock is taken for PCR after each round of DSC.

The subject invention concerns a novel method for the detection of a sequence that is only present in one DNA sample when it is compared with another where such a sequence is absent. The principle of the subject invention is based on the assumption that the maximum efficiency of a subtractive process depends on the contrast ratio of the DNA that is used to subtract (driver, non-adaptor-tagged-amplicon) to the DNA being subtracted (tester, adaptor tagged amplicon). In order to achieve a high driver to tester ratios, a strategy is applied such that converts testers to homologous drivers after each subtractive round. This "negative enrichment" process is accomplished by removing the primers from both ends of the testers by nuclease specific for single stranded DNA after they cross-anneal to drivers (FIG. 1). In the subsequent cyclings of the same procedure, the testers without primers will become drivers, and serve to convert more testers to drivers from the tester population. The result is a double exponential decrease in the copy number(s) of tester species that have homologous counterparts in the driver population and a corresponding increase in the copy number(s) of the driver species (see table I for mathematics evaluation). We term this process as "negative amplification". Presumably, if $10^9$ copies of a target sequence presence in one population is to be eliminated ($Y_e<1$, see Table I for definition) in order to achieve subtraction, then, in the presence of 99 fold (y=$10^{11}$, A=1/100) copies of the correspondent driver, it needs to take 3 (n=2.46) rounds of negative amplification to achieve complete elimination of this tester. This negative amplification process achieves two goals: i) by complete removal of the primers from the unwanted sequences, it eliminates any possible amplification while preserving the rare DNA sequences. This will improve the subtraction sensitivity and efficiency, and produce cleaner products (less false positive results); ii) by bypassing the need for positive enrichment processes between hybridizations, it dramatically simplifies and speeds up the subtractive process.

As used herein, the term "target" DNA or nucleic acid refers to that polynucleotide material to be different between the two tested DNA samples. The term "non-target" refers to that polynucleotide material that is present in both tested DNA samples.

TABLE I

Mathematical model of "negative ampliciation".

| DSC round(s) | Tester copy(ies) | Driver copies | Testers/Total ratios |
|---|---|---|---|
| 0 | 1,000,000 | 1,000,000 | 1/2 |
| 1 | 500,000 | 1,500,000 | 1/4 |
| 2 | 125,000 | 1,875,000 | 1/16 |
| 3 | 7,812.5 | 1,992,187.5 | 1/256 |
| 4 | 30.5 | 1,999,969.5 | 1/65,536 |
| 5 | ~0 | ~2,000,000 | 1/4,294,967,296 |

Hypothetical results of DSC, assuming the starting tester/driver ratio is 1. The survival number(s) of tester after each round of DSC follows the probability of tester to self-anneal in the preceding round, which is ½ before round 1 of DSC, ¼ after round 1, 1/16 after round 2, 1/256 after round 3, 1/65536 after round 4, . . . , and $\frac{1}{2}2^n$ after n rounds. Therefore, the survival copy(s) of tester can be predicted by equation $Y_e = y_A 2^n$, where $Y_e$=probable copy number(s) of survived tester after n round(s) of DSC; y=total copy number(s) of a tester species and its relevant driver; A=probability for tester(s) to self-anneal before the first round of DSC. Similarly, the number(s) of tester conversion to driver in each round of DSC follows the probability of tester to cross anneal with driver, which is ½ before round 1 of DSC, ¾ after round 1 of DSC, 15/16 after round 2, 255/256 after round 3, 65535/65536 after round 4, . . . , and $1\frac{1}{2}2^n$ after n rounds. The copies of driver that survive each round of DSC can be predicted by equation $Y_{or} = y(1 - {}_A2^n)$, where $Y_{or}$ denotes total copy number(s) of driver after n round(s) of DSC. The probability for complete elimination of a tester species can be assessed $[1 - y_A 2^n]$.

(B) Procedure for Differential Subtraction Chain (a) Amplicon Generation (Step A in All Drawings)

Amplicon generation is required for the subject invention to compared the genome of one cell with another, but is optional for comparing the gene expressions of one cell with another. When genomic DNAs or mRNAs of two cell types are compared against each other. One to five micrograms of genomic DNA or cDNA from each sample are digested with restriction enzyme BglII (for genomic DNA) or HindIII (for genomic DNA) or BamHI (for genomic DNA) or DpnII (for cDNA) for 3–6 hours. The digestion products are purified by Qiaquick purification kit (Qiagene, Calif.). For amplicon generation, the purified restriction products are mixed with adapter/primer.

For HindIII restricted DNA fragment, it is ligated with adapter polynucleotide sequences HindIa (SEQ ID 1) and HindIb (SEQ ID 2), or with adapter polynucleotide sequences HindIIa and HindIIb. For BglII restriction DNA fragment, it is ligated with adapter oligonucleotide sequences BgIa (SEQ ID 5) and BgIb (SEQ ID 6) or BgIIa (SEQ ID 7) and BgIIb (SEQ ID 8). For BamHI digested DNA fragment, it is ligated with adapter polynucleotide sequences BamIa (SEQ ID 9) and BamIb (SEQ ID 10) or BamIIa (SEQ ID 11) and BamIIb (SEQ ID 12) (Table II). The criteria for selection of adapter sequence are based on the analysis that the sequence lacks repeat or inverted repeat, is free of significant secondary structure, and has a GC content between 50–60 in the sequence. The selection of an adapter sequence is liberal, and can be a subject of change by individual artisan practicing the subject invention.

When cDNA is the subject of comparison, DNA fragments will be digested a 4 cutter restriction enzyme, since it will generate a cut in every 256 bp, and therefore should generate at least two cuts in most cDNA species. DpnII is selected in this protocol because its cutting pattern produces a 4 bases overhang in the 5' end. This muti-base overhang generally makes it easier to ligate into an adapter. Other 4 or 5 cutter enzymes with 5' or 3' overhang, or even blunt end cutting pattern can also be considered, but the design of adapter should be changed accordingly so as to accommodate individual restriction enzyme cutting pattern.

The DNA fragments and oligonucleotide adapter sequences are mixed. The mixture is heated to 72° C. for 3 minutes, and cooled to 4° C. in 10 minutes (in a PCR machine). The annealed products are ligated with effective amount of reagents. The reagents can be DNA ligase or RNA ligase of any kind, again depending on individual artisan's preference. The ligation products are purified by Qiaquick PCR purification kit. This kit is recommended because of generally fast and reliable recovery of DNA samples. Certainly, there are other ways to eliminate the unwanted enzymes and oligonucleotides, and they also produce excellent results. The decision is entirely up to individual artisan. Alternatively, directly subjecting the ligation mixture to PCR can yield good results, too, albeit a little less consistent.

The ligation products are mixed with all PCR reaction ingredients except Taq polymerase, and heated to 75° C. for 2–10 minutes to release the unligated oligonucleotides. Taq polymerase is subsequently added for 5 minutes at 75° C. to fill in the sticky ends of the adaptors, and followed by PCR to generate amplicons (94.5° C. for 1 minutes, then, for 35 cycles: 94.5° C. 30 seconds, 68° C. for 3 minutes). Heating the mixture to 75° C. before PCR is critical, because this will allow the unligated sequence in the adapter that is attached to the DNA fragment by non-covalent bonds to be released. Such maneuver allows the Taq polymerase added later to fill in the 24 base 5' overhang for the adapter. This fill-in gives the adapter full 24 base pair strength, and enable the attached DNA fragment amplifying in the subsequent PCR.

(b) Differential Subtraction Chain

As I mention earlier, DSC is a cycling procedure for eliminating amplifible homologous sequences between two comparing DNA pools. In each cycle of DSC, it comprises two components: one round of hybridization (Step B in all drawings) and one treatment of nuclease specific for single-stranded DNA (Step C in all drawings).

For hybridization (Step B), the ratio of driver to tester is adjustable based on the absolute number of a targeted

TABLE II

| NAME | | SEQUENCE | SEQ ID |
|---|---|---|---|
| ADAPTER/PRIMER | HindIa | AGCACTCTCCAGCCTGGCTGACGT | 1 |
| ADAPTER | HindIb | AGCTACGTCAGC | 2 |
| ADAPTER/PRIMER | HindIIa | ACCGACGTCGACTATCTCTGGCAT | 3 |
| ADAPTER | HindIIb | AGCTATGCCAGA | 4 |
| ADAPTER/PRIMER | BgIa | AGCACTCTCCAGCCTCTCGTGACC | 5 |
| ADAPTER | BgIb | GATCGGTCACGA | 6 |
| ADAPTER/PRIMER | BgIIa | ACCGACGTCGACTATCAGACGCTT | 7 |
| ADAPTER | BgIIb | GATCAAGCGTCT | 8 |
| ADAPTER/PRIMER | BamIa | ATGAAGTGCACCCTACGATTCGAG | 9 |
| ADAPTER | BamIb | pGATCCTCGAATCGTAGGGTGCACT | 10 |
| ADAPTER/PRIMER | BamIIa | ATGAGACATGTTTCGTAGCCTAGG | 11 |
| ADAPTER | BamIIb | pGATCCCTAGGCTACGAAACATGTC | 12 |
| PRIMER | Oligo d(T) | TTTTTTTTTTTTTTTTTTTTTTTTV | 13 |
| ADAPTER | BgIIIG | ACGCATCAGTGACAATCGACAGCAGGG | 14 |
| Primer | BgIII | ACGCATCAGTGACAATCGACAGCA | 15 | testers. The smaller the representation of a targeted tester species, the lower the ratios of driver/tester should be used in hybridization. This will prevent the complete loss of unique but rare tester species due to incomplete hybridization or non-specific activity of nuclease, and increase the sensitivity of DSC. Theoretically, even when the driver/tester ratio is reduced to 1, it only takes 5 cycles of DSC to eliminate all the amplifiable tester sequences that have homologous counterparts in the driver. Thus, the ratios of driver to tester in DSC hybridization can vary widely, and the number of cycles of DSC is a function of driver/tester ratio.

Generally speaking, ten micrograms of restriction enzyme digested (6–10 hours) driver DNA and 100 ng of tester DNA are mixed together to achieve 100:1 driver/tester ratio. Under this condition, less than 3 rounds of DSC are required to achieve complete subtraction of amplifiable homologous (relative to driver) testers. If the desired products are not turned out, lower ratios should be adjusted.

Figure 2:
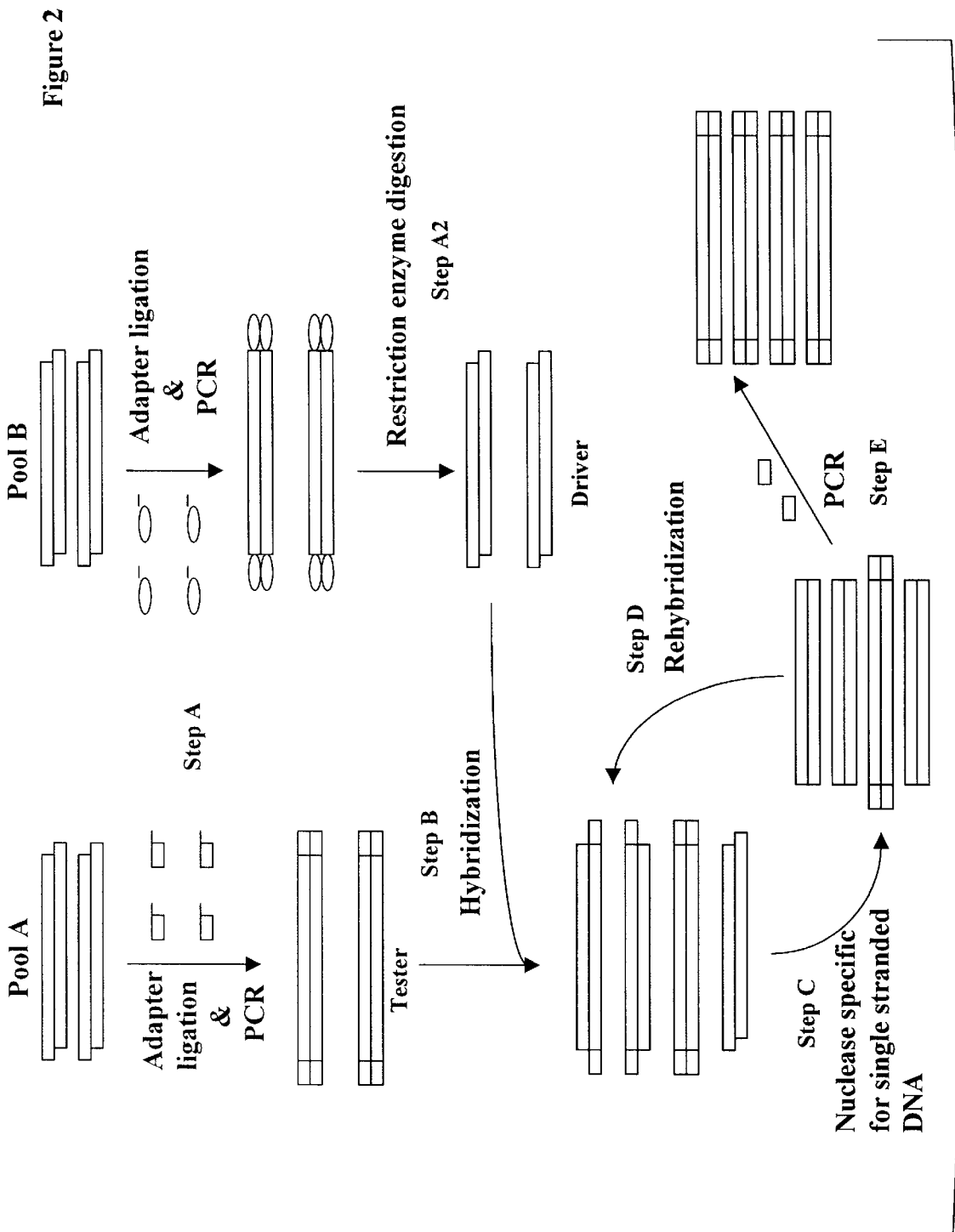
FIG. 2. Scheme of Differential Subtraction Chain when different adapter is used for Pool A and Pool B DNA. Digestion of Drivers is applied before hybridization.
Figure 3:
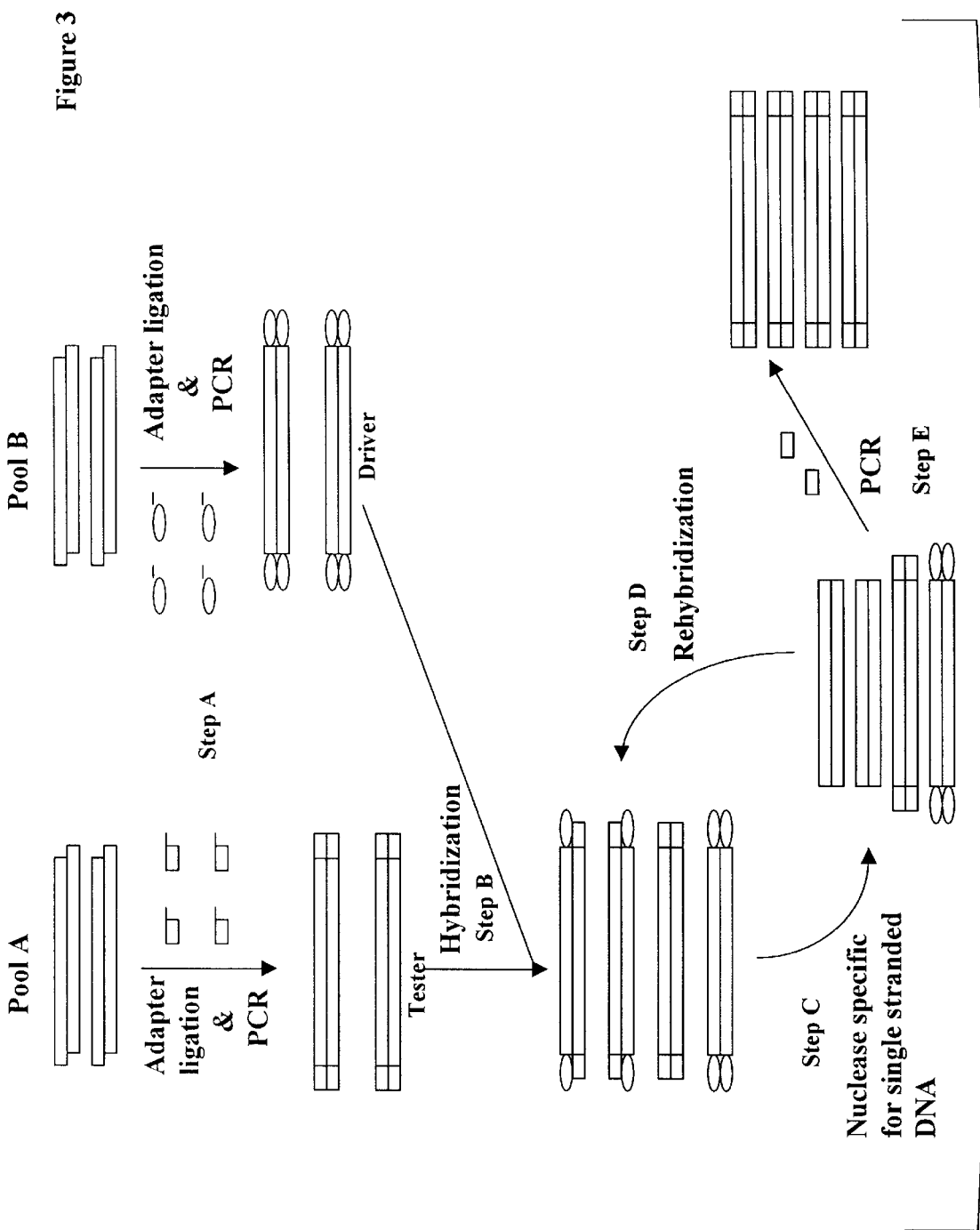
FIG. 3. Scheme of Differential Subtraction Chain when different adapters are used for Pool A and Pool B DNA. No digestion of drivers is applied before hybridization.

Drivers in DSC are usually obtained through digestion of amplicons with the restriction enzyme (Step A2) that is used to generate the same amplicons. Unlike other methods, such as RDA or SSH, where complete removal of adapter from amplicon drivers is essential for a reasonable specificity, the digestion in DSC is less critical. This is particularly true if different sets of adapter sequences are used to generate amplicons for testers and drivers (FIG. 2 and FIG. 3). In DSC, even as high as 10–20% adapter is not removed from drivers, there is still ample cushion to achieve complete subtraction within three rounds, because negative amplification generates an enormous synchronization function. Furthermore, if different adapters are used for testers and drivers, the adapter sequences of tester/driver hybrid will generate mismatched sequence, and will be recognized as single stranded DNA and be degraded by nuclease specific for single stranded DNA. In fact, in some situation, there is no need to use restriction enzyme to digest driver amplicons (FIG. 3), although this may reduce the efficiency of nuclease specific for single stranded DNA to remove adapter sequence, and additional cycles of DSC may be needed to carry the subtraction to completion.

At the beginning of Step B, the DNA of the mixture is denatured by heating to 100° C. for at least 5 minutes to ensure complete denaturing of DNA. Incomplete denaturing of testers that have counterparts in the driver pool is one of the major sources for background. The mixture of tester and driver is hybridized in 3×EE buffer and 1M Sodium Chloride in a volume preferably less than 50 μl. Sufficient time should be allowed to carry the hybridization to completion. Failure to do so may reduce the sensitivity of the subtraction, because un-hybridized single-stranded testers are destroyed in subsequent nuclease treatment. Alternatively, addition of hybridization enhancing agents such polyethylene glycol or dextran sulfate may help to accelerate hybridization, and shorten the timing for each DSC cycle.

At the beginning of Step C, the hybridization products are purified by Qiaquick PCR purification kit to remove the salt. The purified DNAs are digested with nuclease specific for single stranded DNA. The Mung bean nuclease is preferred, because it does not contain the activity to degrade opposing stand DNA from a nicked double stranded DNA like S1 nuclease. The digestion of single stranded adapter sequence with Mung Bean nuclease is carried out at 30° C. for 30 minutes to minimize its intrinsic double stranded DNA nuclease activity.

Figure 6:
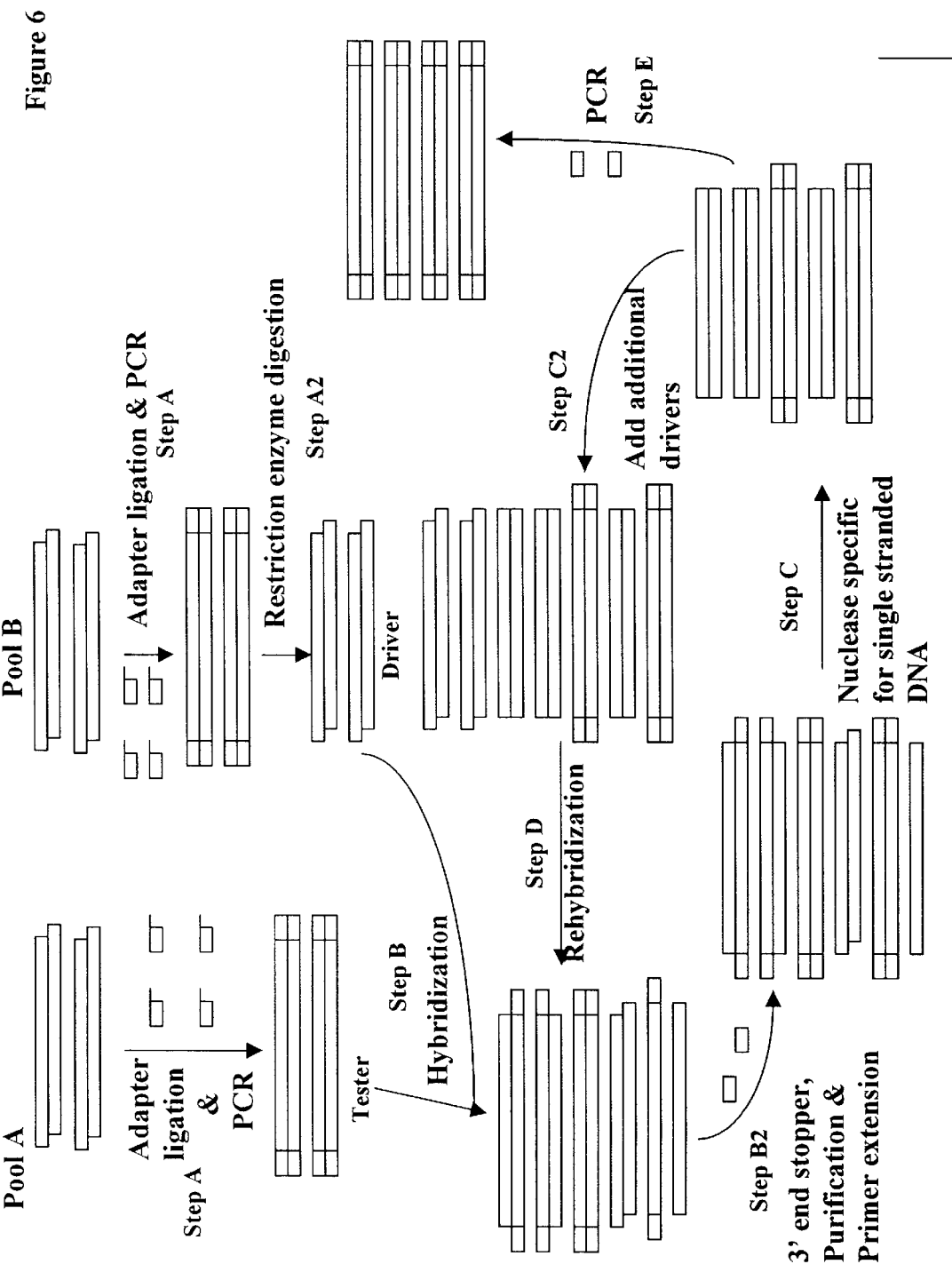
FIG. 6. Scheme of Differential Subtraction Chain with enhancing sensitivity targeting at recovery of un-hybridized tester.
Figure 7:
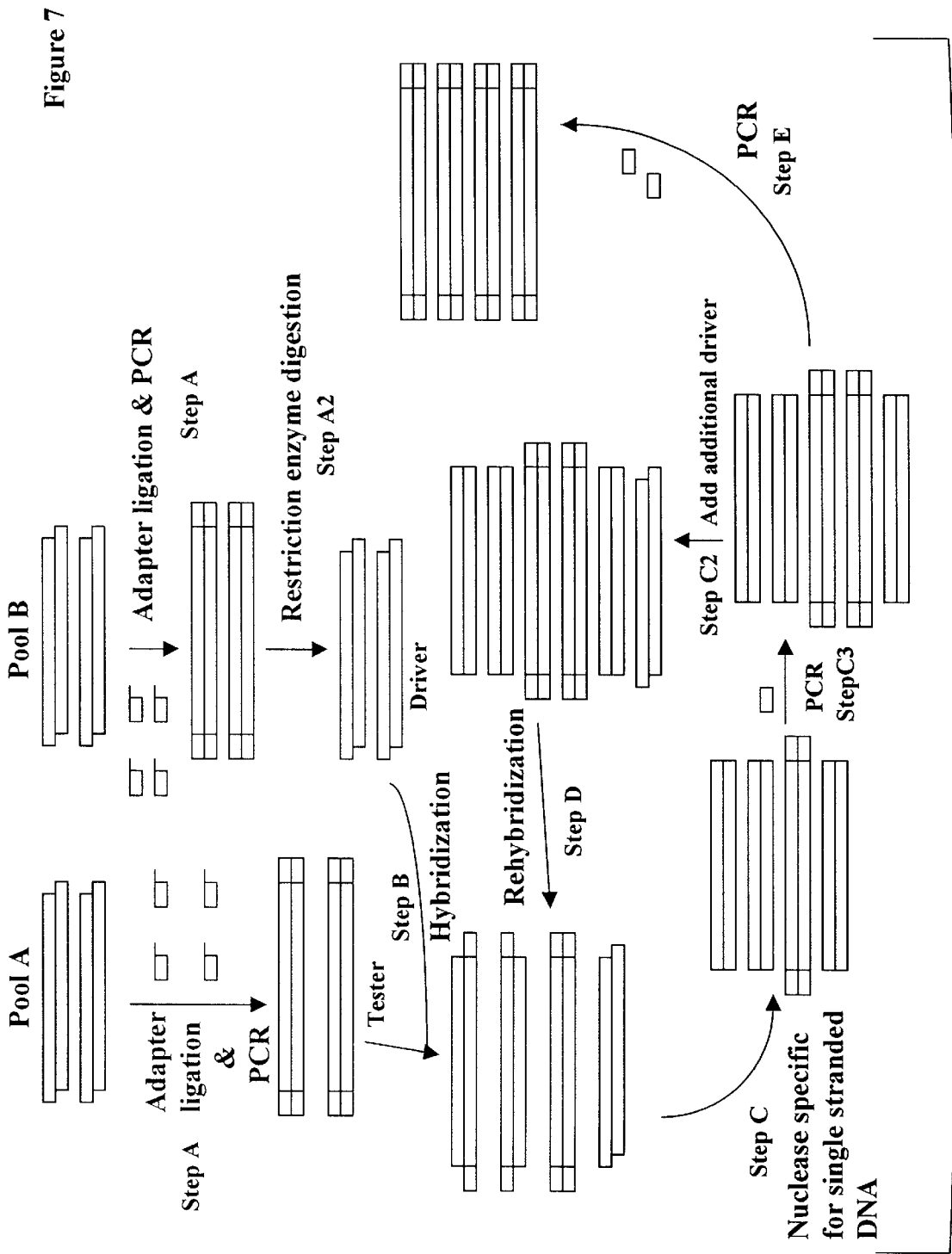
FIG. 7. Scheme of Differential Subtraction Chain with enhancing sensitivity targeting at recovery of rare hybridized tester.

When targeted tester species are extremely rare, such as sequences that are less than 100 copies in 100 ng tester sample, there is a possibility that these sequences are lost during the cycles of DSC. There are two potential sources where a rare tester is lost irreversibly, i.e. incomplete hybridization and minute intrinsic double stranded DNA nuclease activity of Mung bean nuclease. Increase the absolute quantities of overall testers by reducing the drivers/testers ratios will increase the sensitivity. In addition, a modification of DSC can be made to increase its sensitivity (FIG. 6). To overcome a potential incomplete hybridization, which occurs most likely for rare species in hybridization, a 3' extension stopper, such as nucleotide homologues arabinoside or dideoxynucleotide, is introduced into an extension reaction with polymerase after the hybridization step. After the reaction reagents are removed from the solution, excessive primer specific for testers is added with sufficient reagents for primer extension. The extension enzymes could be Taq polymerase, T4 polymerase, Klenow polymerase, or any other kind of DNA polymerase (Step B2 of FIG. 6, also see protocol D for detailed manipulation). The purpose of these two steps of maneuver is to rescue any possible un-hybridized, single stranded tester sequence. Since the overall tester quantity is enriched by such primer extension, additional drivers should be added in the next round of DSC in order to maintain appropriate driver/tester ratio (Step C2 of FIG. 6). To prevent a higher background due to such tester enrichment, stopping the primer extension in driver/tester hybrid by nucleotide homologue is the most critical. This is because a driver to a partial tester (driver with one adapter) conversion will occur if primer extension is not stopped in this condition. An alternative modification of DSC to increase the sensitivity is to modify the DSC scheme in FIG. 3, i.e. driver with intact adapters that are different from the tester's hybridizes with tester. However, before adding nuclease to remove the unmatched adapter sequences in tester/driver hybrid, primer extensions for both tester and driver is performed using primer specific for tester and driver, respectively, to rescue un-hybridized, single stranded tester and driver. Such modification has the appeal of having fewer steps than the other one. S1 nuclease is recommended in the following step to enhance digestion efficiency. The third way to enhance sensitivity of DSC is to enrich tester by short (1–10 cycles) PCR using primer specific for adapter attached to testers after the tester/driver mixture being treated with nuclease specific for single stranded DNA (Step C3 of FIG. 7). This modification emphasizes on recovery of rare testers that have been self-annealed in the hybridization, and prevent lost of these tester during subsequent procedure.

To reduce the possibility that rare tester sequences are degraded due to minute intrinsic double stranded DNA nuclease activity of Mung bean nuclease or S1 nuclease, "carrier DNA" such as lambda phage or salmon sperm DNA can be added into the digestion reaction stock. Alternatively, less than optimal quantity of nuclease may be used to reduce its non-specific activity.

After hybridization mixture is treated with nuclease specific for single stranded DNA. Nuclease has to be inactivated and removed from the reaction. If using Mung bean nuclease, this can be accomplished by treating the mixture with low concentration sodium dodecyl sulfate (SDS). It is optional in terms of purification of the digestion products. When one prefers to do purification, DNA can be purified with phenol. chloroform and ethanol. It can also be purified using other commercially available methods, such as Qiaquick PCR purification kit.

It is highly recommended, though not required, that an aliquot (5–10%) of the digestion products is taken for PCR to examine the subtraction efficiency for each cycles of DSC (Step E). The remainder should be reheated to 100° C. for second round hybridization (Step D). For standard DSC, no additional driver is added after the first round of DSC. PCR is required to amplify the target sequence at the last cycle of DSC. The PCR is performed using thermo-stable polymerase for 30–43 cycles.

A variety of DNA polymerases can be used during PCR with the subject invention. Preferably, the polymerase is a thermostable DNA polymerase that can be obtained from a variety of bacterial species, including *Thermus aquaticus* (Taq), *Thermus thermophilus* (Tth), *Thermus filiformis, Thermus flavus, Thermococcus literalis,* and *Pyrococcus furiosus* (Pfu). Many of these polymerases may be isolated from the bacterium itself or obtained commercially.

Figure 4:
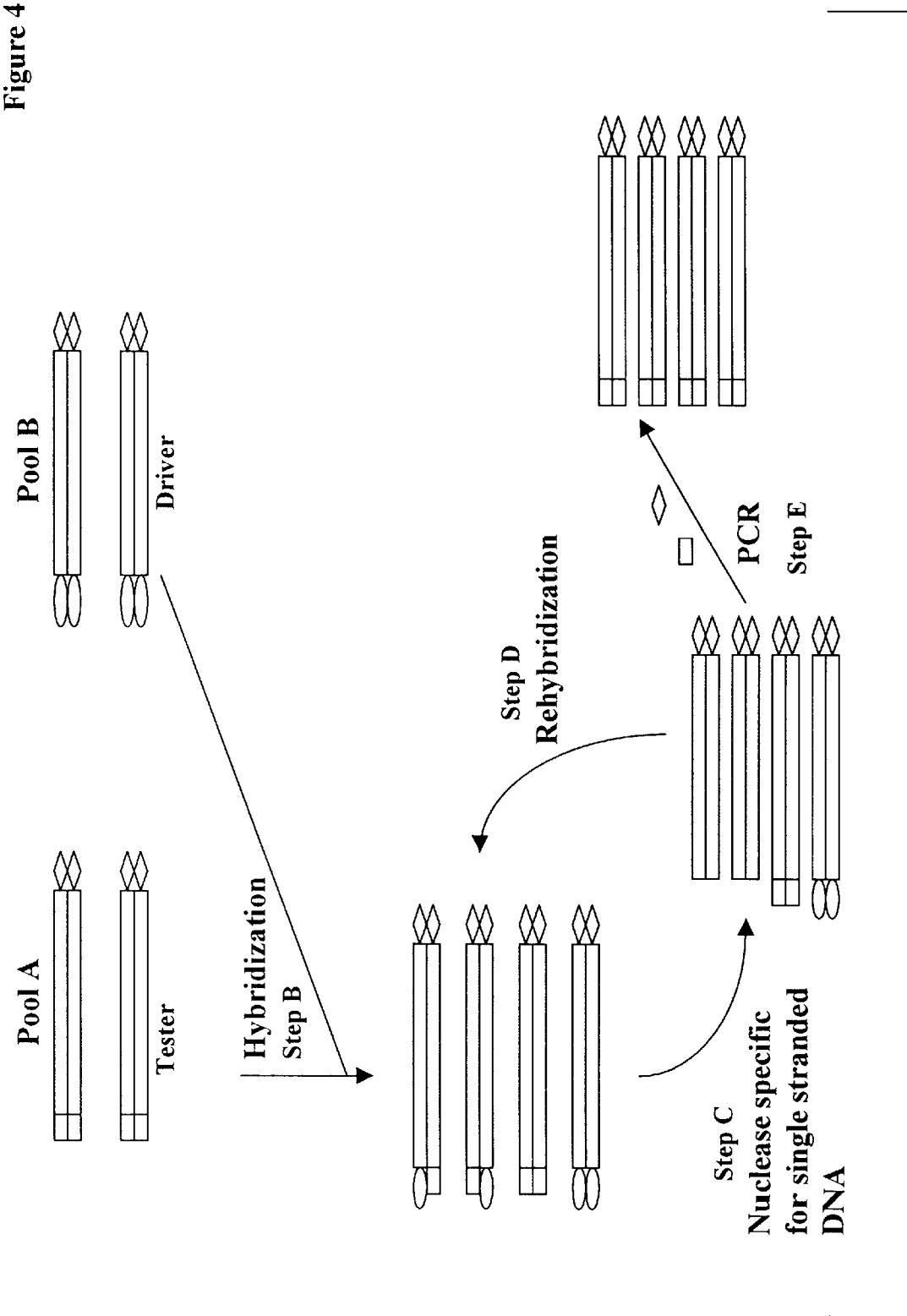
FIG. 4. Scheme of Differential Subtraction Chain when different adapters are used in the same DNA fragment, and the 5' adapters are different between Pool A and Pool B DNA. This scheme is particularly suitable for full length cDNA subtraction.
Figure 5:
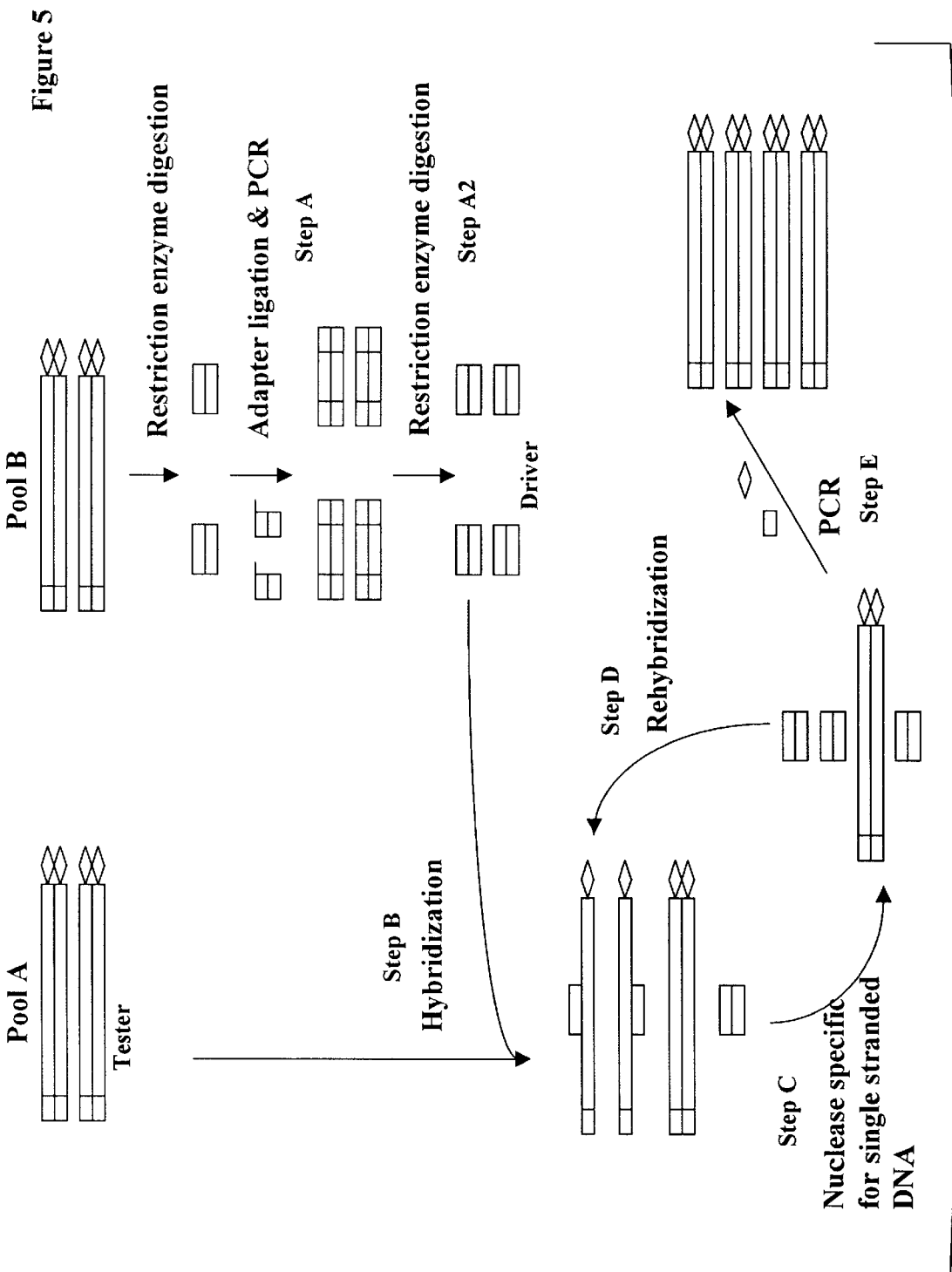
FIG. 5. Scheme of Differential Subtraction Chain when unequal sizes of testers and drivers are hybridized.

A modification on the testers in DSC subtraction should enable DSC to identify the difference of full length cDNA. Under such modification, instead of using cDNA amplicon fragments as testers, mixture of full length cDNAs are used as testers. These full length cDNAs are subtracted by full length cDNA drivers with different 5' end primer sequence from the tester's (FIG. 4) or by cDNA amplicon drivers (FIG. 5). The principle of negative amplification is similar to those of standard DSC. If a species of these cDNA testers survives several cycles of subtraction, there is a good chance that this species represents a unique sequence that is not present in the driver amplicons. This application is particularly useful for rapid isolation of full length cDNA target sequences, because it bypasses most of the subcloning processes.

When extremely rare full length cDNA is the target sequence, protocol of DSC with enhancing sensitivity should be used. This protocol is very similar to the ones described above, except that adapters may be different at each end of the cDNA, and that no restriction enzyme digestion is required for generating full length cDNA drivers.

The subject invention further concerns kits which contain, in separate packaging or compartments, the reagents such as adapters and primers required for practicing the DSC method of the subject invention. Such kits may optionally include the reagents required for performing PCR reaction, such as DNA polymerase, DNA polymerase cofactors, and deoxyribonucleotide-5'-triphosphates, and reagents required for performing single stranded DNA degradation, such as Mung bean nuclease and Mung bean nuclease cofactors, S1 nuclease and S1 nuclease cofactors. Optionally, the kit may also include vairous polynucleotide molecules, DNA or RNA ligases, restriction endonucleases, reverse transcriptase, terminal transferases, various buffers and reagents. The kits may also include reagents necessary for performing positive and negative control reactions. Optimal amounts of reagents to be used in a given reaction can be readily benefit of the current disclosure.

The subject invention also concern service that is provided to interested party to obtain differences of species between two DNA samples. Such services may extend to include procedure of reverse transcription, amplicon generation, DSC, PCR, and screening of DSC products.

(C) Protocols

A. Amplicon Generation From Genomic DNA (Step A of All Drawings)

1. Incubate 1 micrograms of purified genomic DNA with 10 unit of BamH1 restriction enzyme at 37 degree centigrade for four to six hours. The mixture format is the following:

| | |
|---|---|
| DNA (1 microgram per microliter) | 1 microliter |
| One phor all 10× buffer (pharmacia) | 3 microliters |
| Distilled water | 25 microliters |
| Bam H1 (pharmacia) | 1 microliter |

2. Purification of DNA fragments with QIAquick PCR purification kit (Qiagen, Calif.):
   A. Add 150 microliter of Buffer PB to mixture obtained from prior step
   B. Place a QIAquick spin column in a 2 milliliters collection tube.
   C. Apply the sample obtained after (A) to the QIAquick column and centrifuge 30 seconds.
   D. Discard flow-through and place QIAquick column back into the same tube.
   E. Add 0.75 milliliter buffer PE to column and centrifuge 30 second.
   F. Discard flow-through, and place QIAquick column back in the same tube.
   G. Centrifuge for 1 minute.
   H. Place QIAquick column in a clean 1.5 milliliter microfuge tube.
   I. Add 30 microliter buffer EB to the center of the QIAquick column
   J. Centrifuge for 1 minute.

3. Add adapter sequences:

| | | |
|---|---|---|
| For one DNA sample, add: | BamIa (200 micromole per liter) | 5 microliters |
| | BamIb (200 micromole per liter) | 5 microliters |
| | DNA from step 2 | 30 microliters |
| For another DNA sample, add: | BamIIa (200 micromole per liter) | 5 microliters |
| | BamIIb (200 micromole per liter) | 5 microliters |
| | DNA from step 2 | 30 microliters |

4. Incubate the mixture from step 3 at 75 degree centigrade for 3 minutes, cool to room temperature for 5 minute.

5. Add 5 microliter 10×T4 DNA ligase buffer (New England Biolab) and 1 microliter of T4 DNA ligase (400 units per microliter, New England Biolab).

6. Incubate mixture from step 5 at 25 degree Centigrade for 2 hours.

7. Repeat step 2 on the mixture obtained from step 6.

8. In a PCR tube (0.5 milliliter volume), add:

| | |
|---|---|
| 10 × PCR buffer (100 millimole per liter Triezma pH 8.3, 500 millimole per liter potassium chloride) | 5 microliters |
| dNTP mix (10 millimole of each, dATP, dCTP, dGTP, dTTP) | 1 microliter |
| BamIa | 2 microliters |
| Ligation mix from step 7 | 25 microliters |
| Distilled water | 17 microliters |

9. Incubate in thermocycler at 75 degree centigrade for 3 minutes.

10. Add 0.5 microliter Taq polymerase (5 units per microliter) to mixture from step 9 while temperature is maintained at 75 degree centigrade.

11. Incubate mixture from step 10 at 75 degree centigrade for 10 minutes.

12. Incubate mixture from step 11 at 94 degree centigrade for 1 minute.

13. Thermocycle the mixture for 35 cycles from step 12 in the following format: 94 degree centigrade for 15 seconds, 68 degree centigrade for 3 minutes.

B. Amplicon Generation From mRNA (Step A of All Drawings)

1. Add 0.5 micrograms of mRNA or 1 micrograms of total RNA with 1 microliter of oligo d(T) (200 micromole per liter, SEQ ID 13) and 1 microliter BGIIIG (200 micromole per liter, SEQ ID 14).
2. Incubate mixture from step 1 at 75 degree centigrade for 2 minutes.
3. Cool temperature to 4 degree centigrade for 3 minutes.
4. Add to the mixture from step 3 with the following:

| | |
|---|---|
| DTT (20 millimoles per liter) | 1 microliter |
| 5× first strand buffer (Life biotechnology, MD) | 2 microliters |
| dNTP mix (10 millimoles per liter of each dATP dCTP, dGTP, dTTP) | 1 microliter |
| Superscript II (Life Technology) | 1 microliter |

5. Incubate at 42 degree centigrade for one hour.
6. Add in a PCR tube (0.5 milliliter volume):

| | |
|---|---|
| 10 × PCR buffer (Clonetech, CA) | 5 microliters |
| dNTP mix (10 millimole of each, dATP, dCTP, dGTP, dTTP) | 1 microliter |
| Oligo d(T) (200 micromole per liter) | 1 microliter |
| BglIII (200 micromole per liter, SEQ ID 15) | 1 microliter |
| First strand cDNA from step 5 | 2 microliters |
| Distilled water | 39 microliters |
| Ken Taq advantage Polymerase (Clonetech, CA) | 1 microliter |

7. Incubate at 94 degree centigrade for 1 minute.
8. Thermocycle the mixture from step 7 for 25–35 cycles in the following format: 94 degree centigrade for 15 seconds, 56 degree centigrade for 1 minutes, 72 degree centigrade for 4 minutes.
9. In a 1.5 milliliter tube, add:

| | |
|---|---|
| DpnII 10 × buffer | 5 microliters |
| Mixture from step 8 | 5 microliters |
| Distilled water | 38 microliters |
| DpnII (New England Biolab) | 2 microliters |

10. Incubate the mixture from step 9 at 37 degree centigrade for 3 hours.
11. Purification of DNA fragments with QIAquick PCR purification kit (Qiagen, Calif.):
   A. Add 150 microliter of Buffer PB to mixture obtained from prior step.
   B. Place a QIAquick spin column in a 2 milliliters collection tube.
   C. Apply the sample obtained after (A) to the QIAquick column and centrifuge 30 seconds.
   D. Discard flow-through and place QIAquick column back into the same tube.
   E. Add 0.75 milliliter buffer PE to column and centrifuge 30 second.
   F. Discard flow-through, and place QIAquick column back in the same tube.
   G. Centrifuge for 1 minute.
   H. Place QIAquick column in a clean 1.5 milliliter microfuge tube.
   I. Add 30 microliter buffer EB to the center of the QIAquick column
   J. Centrifuge for 1 minute.

12. Add adapter sequences:

| | | |
|---|---|---|
| For one DNA sample, add: | BamIa (200 micromole per liter) | 5 microliters |
| | BamIb (200 micromole per liter) | 5 microliters |
| | DNA from step 11 | 30 microliters |
| For another DNA sample, add: | BamIIa (200 micromole per liter) | 5 microliters |
| | BamIIb (200 micromole per liter) | 5 microliters |
| | DNA from step 11 | 30 microliters |

13. Incubate the mixture from step 12 at 75 degree centigrade for 3 minutes, cool to room temperature for 5 minute.
14. Add 5 microliter 10×T4 DNA ligase buffer (New England Biolab) and 1 microliter of T4 DNA ligase (400 units per microliter, New England Biolab).
15. Incubate mixture from step 14 at 25 degree Centigrade for 2 hours.
16. Repeat step 11 on the mixture obtained from step 15.
17. In a PCR tube (0.5 milliliter volume), add:

| | |
|---|---|
| 10 × PCR buffer (100 millimole per liter Triezma pH 8.3, 500 millimole per liter potassium chloride) | 5 microliters |
| dNTP mix (10 millimole of each, dATP, dCTP, dGTP, dTTP) | 1 microliter |
| BamIa | 2 microliters |
| Ligation mix from step 16 | 25 microliters |
| Distilled water | 17 microliters |

18. Incubate in thermocycler at 75 degree centigrade for 3 minutes.
19. Add 0.5 microliter Taq polymerase (5 units per microliter) to mixture from step 18 while temperature is maintained at 75 degree centigrade.
20. Incubate mixture from step 19 at 75 degree centigrade for 10 minutes.
21. Incubate mixture from step 20 at 94 degree centigrade for 1 minute.
22. Thermocycle the mixture for 35 cycles from step 11 in the following format: 94 degree centigrade for 15 seconds, 68 degree centigrade for 3 minutes.

C. Standard Protocol For Differential Subtraction Chain (Step A2, B, C, D and E of All Drawings)

1. Add in a clean 1.5 milliliter tube with the following:

| | |
|---|---|
| For cDNA DpnII amplicon drivers | |
| DpnII 10 × buffer (New England Biolab) | 10 microliters |
| cDNA DpnII amplicons (10–40 micrograms) | 50 microliters |
| Distilled water | 30 microliters |
| DpnII (New England Biolab) | 10 microliters |
| For genomic BamHI amplicon drivers | |
| One phor all buffer (Pharmacia) | 10 microliters |
| Genomic BamHI amplicons (10–40 micrograms) | 50 microliters |
| Distilled water | 30 microliters |
| BamHI (Pharmacia) | 10 microliters |

2. Incubate the mixture from step 1 at 37 degree centigrade for 3 hours.
3. Purification of DNA fragments with QIAquick PCR purification kit (Qiagen, Calif.):
   A. Add 500 microliter of Buffer PB to mixture obtained from prior step.

B. Place a QIAquick spin column in a 2 milliliters collection tube.

C. Apply the sample obtained after (A) to the QIAquick column and centrifuge 30 seconds.

D. Discard flow-through and place QIAquick column back into the same tube.

E. Add 0.75 milliliter buffer PE to column and centrifuge 30 second.

F. Discard flow-through, and place QIAquick column back in the same tube.

G. Centrifuge for 1 minute.

H. Place QIAquick column in a clean 1.5 milliliter microfuge tube.

I. Add 30 microliter buffer EB to the center of the QIAquick column

J. Centrifuge for 1 minute.

4. In a clean 1.5 milliliter tube, add:

| | |
|---|---|
| 30 × EE buffer (300 millimole per liter of EPPS [N-(2-Hydroxyethyl)-piperazine-N'-(3-propane-sulfonic acid], 30 millimole per liter EDTA [Ethylenediamine tetraacetic acid], pH 8.0) | 5 microliters |
| Amplicon driver (10 mcrograms) | 34 microliters |
| Amplicon testers (100 nanograms) | 1 microliter |

5. Incubate the mixture from step 4 at 100 degree centigrade for 5 minutes.

6. Add to the mixture from step 5 with 10 microliters of 5 moles per liter sodium chloride while maintaining temperature at 100 degree centigrade 7. Incubate the mixture from step 6 for additional 2 minutes.

8. Cool mixture temperature from step 7 to 65 degree centigrade for 20 hours. 9. Repeat step 3.

10. Add in a clean tube the following reagents:

| | |
|---|---|
| Mung bean nuclease 10 × buffer (New England Biolab) | 5 microliters |
| Mixture from step 9 | 30 microliters |
| Distilled water | 14 microliters |
| Mung bean nuclease (New England Biolab) (10 U/ul) | 1 microliter |

11. Incubate the mixture from step 10 at 30 degree centigrade for 30 minutes.

12. Add to mixture from step 11 with 1 microliter of 1% SDS.

13. Repeat step 3, and save 10 microliters mixture in −20 degree centigrade.

14. Repeat step 4 through 13 twice.

15. In a PCR tube (0.5 milliliter volume), add:

| | |
|---|---|
| 10 × PCR buffer (100 millimole per liter Triezma pH 8.3, 500 millimole per liter potassium chloride) | 5 microliters |
| dNTP mix (10 millimole of each, dATP, dCTP, dGTP, dTTP) | 1 microliter |
| BamIa or BamIIa | 2 microliters |
| DSC mix from step 14 | 2.5 microliters |
| Distilled water | 39 microliters |
| Taq polymerase | 0.5 microliter |

16. Incubate the mixture from step 15 at 94 degree centigrade for 1 minute in a thermcycler.

17. Thermocycle the mixture from step 16 for 35 cycles in the following format: 94 degree centigrade for 30 seconds, 68 degree centigrade for 3 minutes.

D. Differential Subtraction Chain With Enhanced Sensitivity Protocol Targeting at Recovery of Un-Hybridized Tester (Steps A2, B, B2, C, C2, D and E of FIG. 6):

1. Add in a clean 1.5 milliliter tube with the following:

| | |
|---|---|
| For cDNA DpnII amplicon drivers | |
| DpnII 10 × buffer (New England Biolab) | 10 microliters |
| cDNA DpnII amplicons (10–40 micrograms) | 50 microliters |
| Distilled water | 30 microliters |
| DpnII (New England Biolab) | 10 microliters |
| For genomic BamHI amplicon drivers | |
| One phor all1 10 buffer (Pharmacia) | 10 microliters |
| Genomic BamHI amplicons (10–40 micrograms) | 50 microliters |
| Distilled water | 30 microliters |
| BamHI (Pharmacia) | 10 microliters |

2. Incubate the mixture from step 1 at 37 degree centigrade for 3 hours.

3. Purification of DNA fragments with QIAquick PCR purification kit (Qiagen, Calif.):

A. Add 500 microliter of Buffer PB to mixture obtained after step 1

B. Place a QIAquick spin column in a 2 milliliters collection tube.

C. Apply the sample obtained after (A) to the QIAquick column and centrifuge 30 seconds.

D. Discard flow-through and place QIAquick column back into the same tube.

E. Add 0.75 milliliter buffer PE to column and centrifuge 30 second.

F. Discard flow-through, and place QIAquick column back in the same tube.

G. Centrifuge for 1 minute.

H. Place QIAquick column in a clean 1.5 milliliter microfuge tube.

I. Add 30 microliter buffer EB to the center of the QIAquick column

J. Centrifuge for 1 minute.

4. In a clean 1.5 milliliter tube, add:

| | |
|---|---|
| 30 × EEP buffer (300 millimole per liter of EPPS [N-(2-Hydroxyethyl)-piperazine-N'-(3-propane-sulfonic acid], 30 millimole per liter EDTA [Ethylenediamine tetraacetic acid], 10% polyethylene glycol, pH 8.0) | 5 microliters |
| Amplicon driver (10 micrograms) | 34 microliters |
| Amplicon testers (100 nanograms) | 1 microliter |

5. Incubate the mixture from step 4 at 100 degree centigrade for 5 minutes.

6. Add to the mixture from step 5 with 10 microliters of 5 moles per liter sodium chloride while maintaining temperature at 100 degree centigrade.

7. Incubate the mixture from step 6 for additional 2 minutes.

8. Cool mixture temperature from step 7 to 65 degree centigrade for 20 hours.

9. Repeat step 3.
10. Add in a clean tube the following reagents:

| | |
|---|---|
| Mixture from step 9 | 42 microliters |
| 10 × PCR buffer | 5 microliters |
| ddNTP (2.5 mM of each ddATP, ddCTP, ddGTP, ddTTP) | 2 microliters |
| Taq polymerase | 1 microliter |

11. Incubate at 72 degree centigrade for 30 minutes.
12. Repeat step 3.
13. Add in a clean tube the following reagents:

| | |
|---|---|
| Mixture from step 12 | 33 microliters |
| 10 × PCR buffer | 4 microliters |
| dNTP (10 mM of each dATP, dCTP, dGTP, dTTP) | 2 microliters |
| Taq polymerase | 1 microliter |

14. Incubate at 72 degree centigrade for 15 minutes.
15. Add in a clean tube the following reagents:

| | |
|---|---|
| Zinc sulfate buffer (New England Biolab) | 5 microliters |
| Mixture from step 14 | 40 microliters |
| Distilled water | 4 microliters |
| Mung bean nuclease (New England Biolab) (10 U/ul) | 1 microliter |

16. Incubate the mixture from step 10 at 30 degree centigrade for 30 minutes.
17. Add to mixture from step 16 with 1 microliter of 1% SDS.
18. Repeat step 3, and save 10 microliters mixture in −20 degree centigrade.
19. Repeat step 4 through 18 twice.
20. In a PCR tube (0.5 milliliter volume), add:

| | |
|---|---|
| 10 × PCR buffer (100 millimole per liter Triezma pH 8.3, 500 millimole per liter potassium chloride) | 5 microliters |
| dNTP mix (10 millimole of each, dATP, dCTP, dGTP, dTTP) | 1 microliter |
| BamIa or BamIIa | 2 microliters |
| DSC mix from step 18 or 19 | 2.5 microliters |
| Distilled water | 39 microliters |
| Taq polymerase | 0.5 microliter |

21. Incubate the mixture from step 20 at 94 degree centigrade for 1 minute in a thermcycler.
22. Thermocycle the mixture from step 21 for 35 cycles in the following format: 94 degree centigrade for 30 seconds, 68 degree centigrade for 3 minutes E. Differential Subtraction Chain With Enhanced Sensitivity Protocol Targeting at Recovery of Rare Hybridized Tester (Step A2, B, C, C3, D and E of FIG. 7)
1. Add in a clean 1.5 milliliter tube with the following:

| | |
|---|---|
| For cDNA DpnII amplicon drivers | |
| DpnII 10 × buffer (New England Biolab) | 10 microliters |
| cDNA DpnII amplicons (10–40 micrograms) | 50 microliters |

| | |
|---|---|
| *-continued* | |
| Distilled water | 30 microliters |
| DpnII (New England Biolabs) | 10 microliters |
| For genomic BamHI amplicon drivers | |
| One phor all 10 buffer (Pharmacia) | 10 microliters |
| Genomic BamHI amplicons (10–40 micrograms) | 50 microliters |
| Distilled water | 30 microliters |
| BamHI (Pharmacia) | 10 microliters |

2. Incubate the mixture from step 1 at 37 degree centigrade for 3 hours.
3. Purification of DNA fragments with QIAquick PCR purification kit (Qiagen, Calif.):
   A. Add 500 microliter of Buffer PB to mixture obtained after step 1.
   B. Place a QIAquick spin column in a 2 milliliters collection tube.
   C. Apply the sample obtained after (A) to the QIAquick column and centrifuge 30 seconds.
   D. Discard flow-through and place QIAquick column back into the same tube.
   E. Add 0.75 milliliter buffer PE to column and centrifuge 30 second.
   F. Discard flow-through, and place QIAquick column back in the same tube.
   G. Centrifuge for 1 minute.
   H. Place QIAquick column in a clean 1.5 milliliter microfuge tube.
   I. Add 30 microliter buffer EB to the center of the QIAquick column
   J. Centrifuge for 1 minute.
4. In a clean 1.5 milliliter tube, add:

| | |
|---|---|
| 30 × EEP buffer (300 millimole per liter of EPPS [N-(2-Hydroxyethyl)-piperazine-N'-(3-propane-sulfonic acid], 30 millimole per liter EDTA [Ethylenediamine tetraacetic acid], 10% polyethylene glycol, pH 8.0) | 5 microliters |
| Amplicon drivers (10 micrograms) | 34 microliters |
| Amplicon testers (100 nanograms) | 1 microliter |

5. Incubate the mixture from step 4 at 100 degree centigrade for 5 minutes.
6. Add to the mixture from step 5 with 10 microliters of 5 moles per liter sodium chloride while maintaining temperature at 100 degree centigrade.
7. Incubate the mixture from step 6 for additional 2 minutes.
8. Cool mixture temperature from step 7 to 65 degree centigrade for 20 hours.
9. Repeat step 3.
10. Add in a clean tube the following reagents:

| | |
|---|---|
| Mung bean nuclease 10 × buffer (New England Biolab) | 5 microliters |
| Mixture from step 13 | 30 microliters |
| Distilled water | 14 microliters |
| Mung bean nuclease (New England Biolab) (10 U/ul) | 1 microliter |

11. Incubate the mixture from step 10 at 30 degree centigrade for 30 minutes.
12. Add to mixture from step 11 with 1 microliter of 1% SDS.

13. Repeat step 3, and save 10 microliters mixture in −20 degree centigrade

14. Add in a clean tube the following reagents:

| | |
|---|---|
| Mixture from step 13 | 40.5 microliters |
| 10 × PCR buffer | 5 microliters |
| Primer specific for tester | 2 microliters |
| dNTP (10 mM of each dATP, dCTP, dGTP, dTTP) | 2 microliters |
| Taq polymerase | 0.5 microliter |

15. Perform PCR in the following condition: 94° C. for 1 minute, then 1 to 10 cycles of 94° C. for 30 second, 68° C. for 3 minutes.

16. Repeat step 3 through 15 twice.

17. In a PCR tube (0.5 milliliter volume), add:

| | |
|---|---|
| 10 × PCR buffer (100 millimole per liter Triezma pH 8.3, 500 millimole per liter potassium chloride) | 5 microliters |
| dNTP mix (10 millimole of each, dATP, dCTP, dGTP, dTTP) | 1 microliter |
| BamIa or BamIIa | 2 microliters |
| DSC mix from step 15 or 16 | 2.5 microliters |
| Distilled water | 39 microliters |
| Taq polymerase | 0.5 microliter |

18. Incubate the mixture from step 17 at 94 degree centigrade for 1 minute in a thermcycler.

19. Thermocycle the mixture from step 18 for 35 cycles in the following format: 94 degree centigrade for 30 seconds, 68 degree centigrade for 3 minutes.

F. Full Length cDNA Differential Subtraction Chain (Step A2, B, C, D and E of FIG. 5):

1. Add in a clean 1.5 milliliter tube with the following:

| For cDNA DpnII amplicon drivers | |
|---|---|
| DpnII 10 × buffer (New England Biolab) | 10 microliters |
| cDNA DpnII amplicons (10–40 micrograms) | 50 microliters |
| Distilled water | 30 microliters |
| DpnII (New England Biolab) | 10 microliters |

2. Incubate the mixture from step 1 at 37 degree centigrade for 3 hours.

3. Purification of DNA fragments with QIAquick PCR purification kit (Qiagen, Calif.):

A. Add 500 microliter of Buffer PB to mixture obtained after step 1

B. Place a QIAquick spin column in a 2 milliliters collection tube.

C. Apply the sample obtained after (A) to the QIAquick column and centrifuge 30 seconds.

D. Discard flow-through and place QIAquick column back into the same tube.

E. Add 0.75 milliliter buffer PE to column and centrifuge 30 second.

F. Discard flow-through, and place QIAquick column back in the same tube.

G. Centrifuge for 1 minute.

H. Place QIAquick column in a clean 1.5 milliliter microfuge tube.

I. Add 30 microliter buffer EB to the center of the QIAquick column

J. Centrifuge for 1 minute.

4. In a clean 1.5 milliliter tube, add:

| | |
|---|---|
| 30 × EE buffer (300 millimole per liter of EPPS [N-(2-Hydroxyethyl)-piperazine-N'-(3-propane-sulfonic acid], 30 millimole per liter EDTA [Ethylenediamine tetraacetic acid], pH 8.0) | 5 microliters |
| Amplicon drivers (10 micrograms) | 34 microliters |
| Full length cDNA testers (500 nanograms) | 1 microliter |

5. Incubate the mixture from step 4 at 100 degree centigrade for 5 minutes.

6. Add to the mixture from step 5 with 10 microliters of 5 moles per liter sodium chloride while maintaining temperature at 100 degree centigrade 7. Incubate the mixture from step 6 for additional 2 minutes.

8. Cool mixture temperature from step 7 to 65 degree centigrade for 20 hours.

9. Repeat step 3.

10. Add in a clean tube the following reagents:

| | |
|---|---|
| Mung bean nuclease 10 × buffer (New England Biolab) | 5 microliters |
| Mixture from step 9 | 30 microliters |
| Distilled water | 14 microliters |
| S1 nuclease (New England Biolab) | 1 microliter |

11. Incubate the mixture from step 10 at 30 degree centigrade for 30 minutes.

12. Add to mixture from step 11 with 1 microliter of 1% SDS.

13. Repeat step 3, and save 10 microliters mixture in −20 degree centigrade.

14. Repeat step 4 through 13 twice.

15. In a PCR tube (0.5 milliliter volume), add:

| | |
|---|---|
| 10 × PCR buffer (100 millimole per liter Triezma pH 8.3, 500 millimole per liter potassium chloride) | 5 microliters |
| dNTP mix (10 millimole of each, dATP, dCTP, dGTP, dTTP) | 1 microliter |
| BglIII (200 micromole per liter) | 1 microliter |
| Oligo d (T) (200 micromole per liter) | 1 microliter |
| DSC mix from step 14 | 2.5 microliters |
| Distilled water | 39 microliters |
| Taq polymerase | 0.5 microliter |

16. Incubate the mixture from step 15 at 94 degree centigrade for 1 minute in a thermcycler.

17. Thermocycle the mixture from step 16 for 35 cycles in the following format: 94 degree centigrade for 30 seconds, 68 degree centigrade for 3 minutes.

(C) Application of Differential Subtraction Chain

The subject invention can be used in a wide variety of procedures. Several of these procedures are examples:

The subject invention can be used in studies to identify the defect in genomic sequences, such as homozygous or heterozygous deletions, insertion, rearrangement and over-amplification. In this application, when abnormal genomic DNA is used as driver to subtract matched normal counterpart, it identifies deletions or rearrangement in abnormal genome. If normal genomic DNA is used as driver to subtract abnormal counterpart, it identifies amplification or insertion present in the abnormal genome. Such application can help to identify genomic markers for trait or disease.

The subject invention can be used in studies to identify micro-organisms present in tissue samples. This application can be accomplished by subtracting the DNA from tissue suspicious of infected with microorganisms with a "normal control" DNA that is pooled from a group of normal individuals. Because of the possibility of polymorphism in genomic DNA, using cDNA derived from mRNA as the subtracting material should be considered. This may be useful in clinical settings for rapid identification of some of the slow growing microorganisms. It would be particularly useful if most of the genetic sequence of microorganisms have been uncovered. In addition, the subject invention can be applied to identify novel infectious agents in the tissue, particularly those ones being difficult to grow in culture.

The subject invention can be used to identify qualitative as well as quantitative differences of gene expression in a tissue after a specific event. When cells are challenged with chemical reagent, drugs, physical stimulus etc., gene expression pattern may be changed in response to these challenges. In application of the subject invention, when DNA from un-challenged control cells is used as driver to subtract counterpart from challenged cells, it identifies genes whose expressions are up-regulated by the stimulation. If DNA from challenged cells is used as driver, it identifies genes whose expressions are shut off by the challenge. Such application may facilitate identification of genes involved in cell proliferation, immortalization, transformation, differentiation, aging and apoptosis.

The subject invention can be used to identify the differences of gene expression between two different types of tissue. In this application, tissue specific antigen relative to one another can be identified. One example would be to identify differences of gene expression between epithelium of bile duct and of small bowel, since morphologically, these two tissues are very similar but functionally are quite different. Another example of this application is to identify the differences of gene expression between normal breast ductal tissue and breast ductal carcinoma. The differences of gene expression between these two tissues may turn out to be important for identifying a better way to make early diagnosis of breast cancer, and make appropriate treatment. When DNA from normal breast ductal tissue is used as driver to subtract DNA from cancer counterpart, it identifies genes that are uniquely expressed in breast cancer. If DNA from breast cancer is used as driver, it identifies genes that are inactivated in cancer tissue. There will be likely numerous similar applications of the subject invention in this area for identifying tumor specific markers and tissue specific antigens.

The subject invention can be used for polymorphism study in determining paternity based on the differences of genomic subtraction pattern. Polymorphism is the base for determining paternity. Therefore, the subtraction pattern of one individual over the other using the subject invention varies based on their genetic similarity. Generally speaking, the closer the kindred relationship, the more similar in their genetic make up, and thus, the more effective subtraction. In this regard, the subject invention can be used in assessing relative closeness of an individual to one another, and can be used to construct a phylogenetic tree in a group of people.

The subject invention can be applied to identify the genetic differences between two strains of microorganisms. When the behavior of two strains of microorganism of the same species appears to be different, the subject invention can be applied to identify the genetic base for such differences. For example, if a strain of bacteria becomes drug resistant, the subject invention can be applied to identify and to isolate the differences in gene expression (or in bacterial genome) between the drug resistant strain and the drug sensitive strain. New drug can be developed targeting the altered gene expression to overcome the drug resistant trait. Such application may help to develop new antibiotics or new anti-viral drugs.

It should be understood that the examples and embodiments described above are only for illustrative purposes. Various modifications or changes in light thereof will be suggested to persons skilled in the art, and are to be included within the spirit and purview of this application and the scope of the appended claims.

I claim:

1. A method for selective elimination of amplifiable non-targeted DNA sequences in a mixture of nucleic acid fragments, comprising the steps of:
    (a) attaching a nucleic acid fragment to one or more PCR adapters to form an adapter-attached nucleic acid fragment, followed by amplifying said adapter-attached nucleic acid fragment through PCR with primer containing nucleic acid sequence complementary to nucleic acid sequence of said adapter to form adapter-attached nucleic acid tester;
    (b) mixing said adapter-attached nucleic acid tester with a nucleic acid driver that contains no attached adapter or contains attached adapter whose sequence differs from said adapter, to form a nucleic acid mixture;
    (c) denaturing and re-annealing tester/driver nucleic acid mixture;
    (d) adding to said nucleic acid mixture an effective amount of reagents necessary for removing adapter sequence from tester/driver heteroduplex;
    (e) repeating step (c) through (d) at least once, wherein no amplification takes place and no additional driver is added.

2. The method, according to claim 1, wherein said adapter-attached nucleic acid fragment is obtained by digesting a nucleic acid with a restriction endonuclease.

3. The method, according to claim 1, wherein said adapter comprises a primer binding sequence portion.

4. The method, according to claim 1, wherein said adapter is either identical or different for either end of nucleic acid fragment.

5. The method, according to claim 1, where adapter sequences are selected from the group consisting of: HindIa (SEQ ID 1), HindIb (SEQ ID 2), HindIIa (SEQ ID 3), HindIIb (SEQ ID 4), BgIa (SEQ ID 5), BgIb (SEQ ID 6), BgIIa (SEQ ID 7), BgIIb (SEQ ID 8), BamIa (SEQ ID 9), BamIb (SEQ ID 10), BamIIa (SEQ ID 11), BamIIb (SEQ ID 12), and BgIIIG (SEQ ID 14).

6. The method, according to claim 1, wherein primer sequences are selected from the group consisting of: HindIa (SEQ ID 1), HindIIa (SEQ ID 3), BgIa (SEQ ID 5), BgIIa (SEQ ID 7), BamIa (SEQ ID 9), BamIIa (SEQ ID 11), oligo (d)T (SEQ ID 13), and BgIII (SEQ ID 15).

7. The method, according to claim 1, wherein step (b) further comprises mixing said nucleic acid tester having said attached adapter with said nucleic acid driver comprising a nucleotide sequence that is complementary to nucleotide sequence of said nucleic acid tester.

8. The method, according to claim 1, wherein step (b) further comprises mixing said nucleic acid tester with nucleic acid driver of similar or smaller sizes than said nucleic acid tester.

9. The method, according to claim 1, wherein said nucleic acid driver is obtained through restriction enzyme digestion or attaching to adapter comprising a nucleotide sequence that is not complementary to said adapter of said nucleic acid tester.

10. The method, according to claim 1, wherein mixture ratios of said nucleic acid tester to said nucleic acid driver range from 1:1 to 1:500.

11. The method, according to claim 1, wherein step (c) comprises digesting single-stranded extension of adapter sequence attached to said nucleic acid tester with nuclease specific for single stranded nucleic acid fragment.

12. A method for selectively eliminating amplifiable non-target nucleic acid fragment in a mixture of nucleic acid fragments with enhancing sensitivity targeting at recovery of un-hybridized tester, comprising the steps of:
    (a) attaching a nucleic acid fragment to one or more PCR adapters to form an adapter-attached nucleic acid fragment, followed by amplifying said adapter-attached nucleic acid fragment through PCR with primer comprising nucleotide sequence that is complementary to said attached adapter, to form adapter-attached nucleic acid tester;
    (b) binding said adapter-attached nucleic acid tester with a nucleic acid driver that contains no attached adapter or contains attached adapter whose sequence differs from said adapter, to form a nucleic acid mixture;
    (c) adding to said nucleic acid mixture an effective amount of reagents necessary for incorporating a 3' extension stopper to form an un-extendable nucleic acid mixture, followed by complete removal of said 3' extension stopper reagents;
    (d) contact said unhybridized nucleic acid tester from said un-extendable nucleic acid mixture with a nucleic acid primer comprising a nucleotide sequence that is complementary to a nucleotide sequence of said adapter to form a pre-extension nucleic acid mixture;
    (e) adding to said pre-extension nucleic acid mixture an effective amount of reagents necessary for primer extension to form tester-enriched nucleic acid mixture;
    (f) adding to said tester-enriched nucleic acid mixture an effective amount of reagents necessary for removing the adapter sequence from tester/driver heteroduplex to form blunt ended tester-enriched nucleic acid mixture;

(g) cycling said blunt ended tester-enriched nucleic acid mixture through at least one cycle of the steps of (b) through (f);

(h) contacting said nucleic acid tester having said attached adapter from said blunt ended nucleic acid mixture obtained after step (g) with a nucleic acid primer comprising a nucleotide sequence that is complementary to a nucleotide sequence of said attached adapter;

(i) adding to nucleic acid mixture obtained from step (h) an effective amount of reagents necessary for performing a PCR; and, (j) cycling the mixture obtained after step (i) through at least one cycle of the denaturing, annealing and primer extension steps of PCR to obtain an amplification product of said nucleic acid tester that did not bind to said nucleic acid driver in step (b).

13. The method, according to claim 12, wherein said primer is complementing to said adapter attached to said nucleic acid tester.

14. The method, according to claim 12, wherein said nucleic acid driver with attached adapter whose sequence differs from said adapter attached to said nucleic acid tester bypasses step (c) in a first cycle.

* * * * *

SEQUENCE LISTING

<160> NUMBER OF SEQ ID NOS: 15

<210> SEQ ID NO: 1
<211> LENGTH: 24
<212> TYPE: DNA
<213> ORGANISM: synthetic
<220> FEATURE:
<221> NAME/KEY: HindIa
<222> LOCATION:

<400> SEQUENCE: 1
agcactctcc agcctggctg acgt                    24

<210> SEQ ID NO: 2
<211> LENGTH: 12
<212> TYPE: DNA
<213> ORGANISM: synthetic
<220> FEATURE:
<221> NAME/KEY: HindIb
<222> LOCATION:

-continued

```
<400> SEQUENCE: 2
agctacgtca gc                                                         12

<210> SEQ ID NO: 3
<211> LENGTH: 24
<212> TYPE: DNA
<213> ORGANISM: synthetic
<220> FEATURE:
<221> NAME/KEY: HindIIa
<222> LOCATION:

<400> SEQUENCE: 3
accgacgtcg actatctctg gcat                                            24

<210> SEQ ID NO: 4
<211> LENGTH: 12
<212> TYPE: DNA
<213> ORGANISM: synthetic
<220> FEATURE:
<221> NAME/KEY: HindIIb
<222> LOCATION:

<400> SEQUENCE: 4
agctatgcca ga                                                         12

<210> SEQ ID NO: 5
<211> LENGTH: 24
<212> TYPE: DNA
<213> ORGANISM: synthetic
<220> FEATURE:
<221> NAME/KEY: BgIa
<222> LOCATION:

<400> SEQUENCE: 5
agcactctcc agcctctcgt gacc                                            24

<210> SEQ ID NO: 6
<211> LENGTH: 12
<212> TYPE: DNA
<213> ORGANISM: synthetic
<220> FEATURE:
<221> NAME/KEY: BgIb
<222> LOCATION:

<400> SEQUENCE: 6
gatcggtcac ga                                                         12

<210> SEQ ID NO: 7
<211> LENGTH: 24
<212> TYPE: DNA
<213> ORGANISM: synthetic
<220> FEATURE:
<221> NAME/KEY: BgIIa
<222> LOCATION:

<400> SEQUENCE: 7
accgacgtcg actatcagac gctt                                            24

<210> SEQ ID NO: 8
<211> LENGTH: 12
<212> TYPE: DNA
<213> ORGANISM: synthetic
<220> FEATURE:
<221> NAME/KEY: BgIIb
<222> LOCATION:

<400> SEQUENCE: 8
```

-continued

```
gatcaagcgt ct                                               12

<210> SEQ ID NO: 9
<211> LENGTH: 24
<212> TYPE: DNA
<213> ORGANISM: synthetic
<220> FEATURE:
<221> NAME/KEY: BamIa
<222> LOCATION:

<400> SEQUENCE: 9
atgaagtgca ccctacgatt cgag                                  24

<210> SEQ ID NO: 10
<211> LENGTH: 24
<212> TYPE: DNA
<213> ORGANISM: synthetic
<220> FEATURE:
<221> NAME/KEY: BamIb
<222> LOCATION:

<400> SEQUENCE: 10
gatcctcgaa tcgtagggtg cact                                  24

<210> SEQ ID NO: 11
<211> LENGTH: 24
<212> TYPE: DNA
<213> ORGANISM: synthetic
<220> FEATURE:
<221> NAME/KEY: BamIIa
<222> LOCATION:

<400> SEQUENCE: 11
atgagacatg tttcgtagcc tagg                                  24

<210> SEQ ID NO: 12
<211> LENGTH: 24
<212> TYPE: DNA
<213> ORGANISM: synthetic
<220> FEATURE:
<221> NAME/KEY: BamIIb
<222> LOCATION:

<400> SEQUENCE: 12
gatccctagg ctacgaaaca tgtc                                  24

<210> SEQ ID NO: 13
<211> LENGTH: 31
<212> TYPE: DNA
<213> ORGANISM: synthetic
<220> FEATURE:
<221> NAME/KEY: oligo d(T)
<222> LOCATION:

<400> SEQUENCE: 13
tttttttttt tttttttttt tttttttttt v                          31

<210> SEQ ID NO: 14
<211> LENGTH: 27
<212> TYPE: DNA
<213> ORGANISM: synthetic
<220> FEATURE:
<221> NAME/KEY: BgIIIG
<222> LOCATION:

<400> SEQUENCE: 14
```

```
acgcatcagt gacaatcgac agcaggg                                          27

<210> SEQ ID NO: 15
<211> LENGTH: 24
<212> TYPE: DNA
<213> ORGANISM: synthetic
<220> FEATURE:
<221> NAME/KEY: BgIII
<222> LOCATION:

<400> SEQUENCE: 15
acgcatcagt gacaatcgac agca                                             24
```